United States Patent [19]

Ritter et al.

[11] Patent Number: 5,244,628

[45] Date of Patent: Sep. 14, 1993

[54] SIMPLIFIED PROCESS FOR STERILIZING SEMI-SOLID TO SOLID PREPARATIONS BASED ON OLIGOMERS OF LOWER HYDROXYCARBOXYLIC ACIDS OR THEIR SALTS

[75] Inventors: Wolfgang Ritter, Haan; Johann-Friedrich Fues, Grevenbroich, both of Fed. Rep. of Germany

[73] Assignee: Henkel Kommanditgesellschaft auf Aktien, Duesseldorf, Fed. Rep. of Germany

[21] Appl. No.: 768,715

[22] PCT Filed: Apr. 19, 1990

[86] PCT No.: PCT/EP90/00627

§ 371 Date: Oct. 28, 1991

§ 102(e) Date: Oct. 28, 1991

[87] PCT Pub. No.: WO90/13319

PCT Pub. Date: Nov. 15, 1990

[30] Foreign Application Priority Data

Apr. 28, 1989 [DE] Fed. Rep. of Germany ....... 3914080

[51] Int. Cl.$^5$ .................................................. A61L 2/12
[52] U.S. Cl. ..................................... 422/21; 422/307; 250/455.11
[58] Field of Search ............ 422/21, 307, 186, 186.04, 422/186.05; 250/455.11, 428; 252/346

[56] References Cited

U.S. PATENT DOCUMENTS

| 4,250,139 | 2/1981 | Luck et al. | 422/21 |
| 4,778,656 | 10/1988 | Allen et al. | 422/20 |
| 4,801,427 | 1/1989 | Jacob et al. | 422/23 |
| 4,818,488 | 4/1989 | Jacob | 422/23 |
| 4,917,586 | 4/1990 | Jacob | 422/21 |
| 4,931,261 | 6/1990 | Jacob | 422/292 |
| 4,943,417 | 7/1990 | Jacob | 422/292 |

Primary Examiner—Robert J. Warden
Assistant Examiner—E. Leigh Dawson
Attorney, Agent, or Firm—Wayne C. Jaeschke; Norvell E. Wisdom, Jr.; Daniel S. Ortiz

[57] ABSTRACT

Described is a process for the simplified sterilization, by heating to high temperatures, of semisolid to solid preparations based on oligomers of lower carboxylic acids or their salts, as well as their transformation products with molecular weight regulating components, the preparations also optionally including biocompatible minerals. According to the invention, the materials to be sterilized are subjected to the action of high frequency oscillations in the microwave range (microwaves).

20 Claims, No Drawings

SIMPLIFIED PROCESS FOR STERILIZING SEMI-SOLID TO SOLID PREPARATIONS BASED ON OLIGOMERS OF LOWER HYDROXYCARBOXYLIC ACIDS OR THEIR SALTS

BACKGROUND OF THE INVENTION

DE-OSS 32 29 540 and 37 16 302 relate to resorbable waxes for mechanically stanching blood on hard, body tissue, particularly on bones, which are characterized in that they consist of polyester oligomers of lower hydroxycarboxylic acids which are viscous to solid and wax-like at body temperature. Corresponding polyesters, oligomers of lactic acid and/or glycolic acid are described as particularly suitable. By virtue of their structure, these waxes can be degraded by the body's own metabolic mechanisms, the degradation rate being adjustable in known manner. The preferred waxes have average molecular weights in the range from about 200 to 1,500 and, more particularly, in the range from about 300 to 1,000.

Monofunctional and/or difunctional alcohols and/or carboxylic acids are used to regulate the average molecular weight, particular significance being attributed to glycerol as a polyfunctional alcohol. In another important embodiment, the resorbable materials are almost completely freed from free carboxyl groups. This may be done either by specific purification, as described for example in the publications cited above, or by salt formation at carboxyl groups which are still present in the reaction product or which have been specifically added, for example through free hydroxycarboxylic acids of the type mentioned.

Thus, earlier German patent applications P 38 25 211.2 (D 8293) and P 38 26 915.5 (D 8265) describe compositions based on oligomers of the described type which are characterized by a content of body-compatible salts of organic and/or inorganic acids, corresponding salts being formed by reaction of any free carboxyl groups still present in the oligomer wax and/or being homogeneously incorporated in the wax as added salts. In the second of these two earlier applications, this concept of body-compatible and resorbable oligomer compounds, particularly based on glycolic acid and/or lactic acid, is widened to the extent that at least partly resorbable bone substitutes and/or bone composites and auxiliaries for fixing prosthesis material in living bone tissue are described. The oligomers used for this purpose may have average molecular weights in a broader range of from about 200 to 10,000 g/mol and, more particularly, in the range from about 300 to 5,000 g/mol. Mixtures of oligomer resins containing ceramic materials in preferably homogeneous distribution are described as particularly suitable. These ceramic materials, which are present in particular in powder and/or granular form, may be resorbable or even non-resorbable in the body, particular significance being attributed to bioactive ceramic materials, above all based on calcium phosphate compounds. Suitable calcium phosphates are, for example, hydroxyl apatite and/or tricalcium phosphate.

The described oligomer compounds are produced by a polycondensation and/or polyaddition reaction carried out at elevated temperature, generally in the presence of small quantities of mildly acidic catalysts. The ceramic materials and/or salts optionally used are also normally incorporated at elevated temperature, generally via the melt phase of the organic resins.

DESCRIPTION OF THE INVENTION

For practical application in the field of surgery, the compositions in question generally have to lend themselves to portion-controlled packing and, at the same time, to complete sterilization. The problem addressed by the present invention was to satisfy these requirements as simply as possible for materials of the described type. The technical solution to this problem is based on the known principle of germ destruction by heating the material to be sterilized to sufficiently high temperatures. The teaching of the invention is crucially dependent upon the choice of the technical said with which temperature control is undertaken and managed for at least considerable periods of the sterilization process. The new teaching is based on the discovery that it is possible to heat the material to be sterilized to the necessary temperatures in a predeterminable manner by the action of high-frequency electromagnetic vibrations in the microwave range—known generally as "microwaves".

Accordingly, the present invention relates to a process for the sterilization of semisolid to solid preparations based on oligomers of lower hydroxycarboxylic acids or salts or reaction products thereof with molecular weight regulators, more particularly monofunctional and/or polyfunctional alcohols or corresponding carboxylic acids, which may even be present in admixture with body-compatible minerals, by heating to elevated temperatures, characterized in that the material to be sterilized is exposed to the effect of microwaves.

The application of high-frequency electromagnetic vibration in the upper megahertz range to the middle gigahertz range has been increasingly put into practice in recent years. One well-known example of this from the domestic field is the microwave oven which is used for the rapid and thorough heating and, optionally, the preliminary defrosting of precooked foods. The selected microwave radiation in the lower to middle gigahertz range, for example in the range from about 0.1 to 300 GHz and preferably in the range from about 0.1 to 30 GHz, excites the water molecules present in the material to be heated and thus heats the water-containing material from inside outwards. The ability of the radiation to penetrate into the interior of the material to be heated is greater at lower frequencies than at higher frequencies within the range mentioned, cf. for example *Mikrowellen* (Günter Nemitz, München, 1980), page 155.

The use of microwaves has also been proposed in related fields, for example for heating damp textiles, particularly in washing and drying processes. In every case, however, the microwaves are used in water-containing, moist material.

On the basis of their production, oligomer resins of the type targeted by the present invention are to be regarded as anhydrous materials. Known materials of this type include not only polycondensation resins having comparatively limited average molecular weights, as targeted by the present invention, but also solid polymers of this type having very much higher molecular weights. Attempts to heat, let alone sterilize, solid high molecular weight materials of this type, for example body-resorbable filament material based on high polymers of glycolic acid and/or lactic acid, by the action of microwaves have been unsuccessful. It would appear that inadequate resonance is initiated between inherently polar parts of the molecule and the radiation.

Surprisingly, the situation takes on a completely different appearance when resins of the type described in the previously published patents and patent applications cited at the beginning, or in older patents and patent applications, are exposed to the effect of microwaves. The radiation of energy in a domestic microwave oven results in comparatively rapid heating of the resins, the temperature of at least about 100° C. that is crucial to sterilization being reached more quickly, the more rapidly the softening and/or liquefaction of the oligomers accompanying this heating occurs. In addition, the radiation of equal amounts of energy into an initially wax-like and solid material which becomes increasingly soft to liquid at increasing temperatures shows that the interaction between the material to be heated and the radiated energy is more effective, the more mobile in character the resin becomes as a result of the increase in temperature. The increases in temperature which the sample of material undergoes and which can be adjusted per predetermined unit of energy and time become greater with increasing softness of the material sample during the stepwise transition from the solid state to the molten state.

One explanation of the suitability of microwaves for thermal sterilization of the class of resins targeted by the invention could be that, even with material samples that are initially wax-like to solid in appearance, sufficient amounts of comparatively short-chain oligomers are present to enter into an interaction with the radiated energy, being heated in the process, softening their immediate surroundings and leading to an increase in the responsive resin volume. Another crucial factor in this regard would appear to be the fact that not only do the microwaves attack the outer regions of the material to be heated, they also penetrate throughout the material as a whole. As a result, the material is completely heated from inside outwards. It is clear that the conditions essential for solving the problem of sterilization addressed by the invention are thus established. This applies not only to materials which are formed as such by the oligomers, for example of glycolic acid and/or lactic acid, but also to the mixed products containing ceramic components which are mentioned in the earlier applications cited above. Where resin and ceramic material—preferably in finely divided form—are thoroughly mixed, even comparatively thick layers of material are heated throughout and, hence, sterilized by the action of microwaves according to the invention. It can be seen that, in practice, this considerably simplifies the provision of portion-controlled packs in fully sterilized form.

According to the invention, therefore, it is thus possible, for example, to subject bone waxes or materials intended as adhesion said for medical purposes to sterilization in individual portions and, more particularly, in the form of at least substantially sealed portion packs. The material to be sterilized is accommodated in the pack which withstands the action of microwaves and allows them to pass through. It is generally known that plastics, for example polyolefins, are particularly suitable for this purpose and are already being widely used, for example, for the portion-controlled packing of so-called instant meals for heating in microwave ovens.

The oligomer materials to be subjected to the process should preferably be at least viscous and free-flowing at temperatures in the range in which the sterilizing treatment is carried out. Bone waxes and adhesives of the described type, particularly those having average molecular weights in the ranges mentioned, are normally molten and free-flowing at temperatures above 100° C., for example at temperatures of up to 130° C.

In one particular embodiment of the invention, it may be useful to activate preparations which are solid at room temperature and which, initially, show little response to the effect of high-energy radiation of the type in question by conventionally preheating materials of this type to a limited extent. It may be useful in this regard to preheat at least parts of the particular samples of material to be sterilized until they begin to soften and then to expose the material thus pretreated to the effect of microwaves. However, a combined temperature treatment such as this is necessary only in special cases.

In the process according to the invention, the microwave radiation may be applied intermittently or continuously and may cover an entire process stage or only parts thereof. The temperature to be established is controlled by the choice of the intensity and duration of the microwave radiation. By intermittent irradiation at comparatively low power levels, for example up to at most 200 watts, it is possible to establish moderate temperatures and/or to keep to a predetermined temperature range for a relatively long period. In the heating phase of the process, it can be useful to apply comparatively high power levels, for example up to 1,000 watts, either continuously or intermittently.

The residence time of the material to be sterilized in the predetermined sterilization temperature range is determined by existing knowledge of sterilization processes of the type required in the context of the invention. For example, sterilization can be obtained by heating to temperatures of at least 100° C. and preferably to temperatures of 110° C. for the period required for safe destruction of unwanted germs. For example, temperatures in the range above 120° C. to 180° C. applied for a few minutes or even longer are suitable.

To carry out the process according to the invention, it is often sufficient to apply a predetermined amount of energy to the quantity of material to be sterilized, which is preferably accommodated in the at least substantially sealed portion pack, and then to leave the correspondingly heated sample of material to cool in a regulated or delayed process. If necessary, the particular portion pack may then be completely sealed without further contact with the material accommodated therein.

EXAMPLES

The microwave generator used is a commercially available microwave oven of the "Siemens" brand which has a timed power input graduated as follows: 90 W, 180 W, 360 W and 600 W. The radiated energy has a frequency of 2.45 GHz.

The material samples characterized in detail in the following Examples are present in quantities of approximately 30 g in unsealed glass bottles which, to carry out the tests, are successively placed at the center of the heating zone.

The starting temperature of all material samples is 21° C., unless otherwise specifically stated. Microwave energy is applied continuously or intermittently as described in the Examples (selected energy input and duration of the particular heating phase). Immediately after a heating phase, the temperature in the upper part of the particular material sample is determined by insertion of a laboratory mercury thermometer. The following heating phase(s) are each carried out immediately after the temperature measurement.

The chemical composition of the oligomers investigated and their physical character both before and after the application of microwave energy are shown in the following Examples.

EXAMPLE 1

Reaction product based on glycerol, glycolic acid and oleic acid in a molar ratio of 1:3:3: viscous and free-flowing at room temperature

| Heating stage | Energy input (W) | Heating time (secs.) | Temperature of the irradiated material °C. |
|---|---|---|---|
| 1. | 600 | 30 | 59 |
| 2. | 600 | 15 | 75 |

The material sample is cooled to an initial temperature of 30° C. and subjected to another two-stage heating cycle. The following results are obtained.

| Heating stage | Energy input (W) | Heating time (secs.) | Temperature of the irradiated material °C. |
|---|---|---|---|
| 1. | 600 | 60 | 78 |
| 2. | 600 | 60 | 131 |

EXAMPLE 2

Reaction product based on glycerol, glycolic acid, lactic acid and oleic acid in a molar ratio of 1:6:6:3. The starting material is highly viscous at room temperature.

| Heating stage | Energy input (W) | Heating time (secs.) | Temperature of the irradiated material °C. |
|---|---|---|---|
| 1. | 600 | 45 | 74 |

The heated material is a thin liquid. It is cooled to a starting temperature of 32° C. and then resubjected to two-stage heating with the following results:

| Heating stage | Energy input (W) | Heating time (secs.) | Temperature of the irradiated material °C. |
|---|---|---|---|
| 1. | 600 | 60 | 76 |
| 2. | 600 | 45 | 113 |

EXAMPLE 3

A condensation product based on glycerol and lactic acid in a molar ratio of 1:4, which is viscous at room temperature, is exposed for 60 seconds to a single-stage power input of 600 W. The final temperature reached is 158° C. The material sample is a thin liquid.

EXAMPLE 4

A viscous starting material based on glycerol and lactic acid in a molar ratio of 1:12 is exposed to two-stage heating. The operating conditions and results are as follows:

| Power input (W) | Time (secs.) | Temperature °C. | Resin consistency |
|---|---|---|---|
| 180 | 60 | 38 | Viscous |
| 600 | 60 | 138 | Thinly liquid |

EXAMPLE 5

A solid, wax-like condensation product based on tallow alcohol and lactic acid in a molar ratio of 1:17 is heated by exposure to a power input of 600 W in three stages. The first stage lasts 50 seconds while the second and third stages each last 60 seconds.

After the first heating stage, the material sample is so solid that its temperature cannot be measured. After the second heating stage, the material sample has softened to such an extent that the thermometer can be inserted into the wax mass. The temperature determined at this stage is 55° C. At the end of the third heating stage, the material is in an inhomogeneous and partly molten state. The temperature in the molten parts is 105° C.

EXAMPLE 6

A solid wax-like condensation product based on glycerol and glycolic acid in a molar ratio of 19 is exposed twice for 30 seconds to a power input of 600 W.

Result of the first treatment stage: the material sample is still mainly solid, but has melted to paste-like state in the middle. A temperature of 74° C. is measured in the melted parts. On completion of the second heating stage, the material is almost completely molten. The temperature measured in the melt is 133° C.

EXAMPLE 7

A viscous/solid condensation product based on glycerol/glycolic acid/lactic acid in a molar ratio of 15:1 is exposed for 45 seconds to a single-stage power input of 600 W. A thinly liquid melt having a temperature of 126° C. is formed.

EXAMPLE 8

A viscous/solid material based on glycerol, glycolic acid and lactic acid in a molar ratio of 1:2:12 is exposed for 60 seconds to a power input of 360 W and then for another 60 seconds to a power input of 600 W.

After the first heating stage, the material sample is viscous and has a temperature of about 38° C. The thinly liquid, molten material obtained in the second heating stage has a temperature of 162° C.

EXAMPLE 9

A glycerol/glycolic acid ester in a molar ratio of 1:3 (consistency: viscous) is exposed for 70 seconds to a single power input of 360 W. A thinly liquid melt having a temperature of 131° C. is formed.

EXAMPLE 10

An oligomeric condensation product based on glycerol, glycolic acid and lactic acid in a molar ratio of 1:6:6 is subjected to a six-stage heating cycle, power input 600 w in each stage, in the following time sequence:

1st stage: 45 secs., resin unchanged, solid and lukewarm
2nd stage: 30 secs., viscous consistency, 39° C.
3rd stage: 20 secs., resin partly molten, temperature in the molten zone 84° C.

4th stage: 10 secs., more melting, temperature in the molten zone 91° C.
5th stage: 10 secs., completely molten and viscous, temperature 94° C.
6th stage: 20 secs., thinly liquid, dripping melt, temperature 119° C.

What is claimed is:

1. A process for the sterilization of a semisolid to solid composition consisting essentially of:
   (A) oligomers having average molecular weights in the range from about 200 to about 10,000, said oligomers consisting essentially of the residues of monomers selected from the group consisting of lower hydroxycarboxylic acids, salts thereof, and mixtures thereof, and, optionally, also of residues of molecular weight regulator monomers; and, optionally
   (B) body-compatible minerals,
said process comprising heating said composition to a sterilization temperature range and maintaining said composition within the sterilization temperature range for an effective time to destroy any unwanted germs present in said composition, said heating being accomplished by irradiating said composition with microwaves.

2. A process as claimed in claim 1, wherein the composition sterilized by the process is viscous to wax-like at body temperature.

3. A process as claimed in claim 1, wherein said composition is sterilized while contained in a portion-controlled pack.

4. A process as claimed din claim 1, wherein the composition that is sterilized is viscous and free-flowing in the sterilization temperature range.

5. A process as claimed in claim 1, wherein the compositions sterilized by the process is solid at room temperature and is exposed to the microwave radiation after being preheated.

6. A process as claimed din claim 1, wherein the composition to be sterilized is continuously irradiated with microwaves for each of at least two distinct periods of time, said periods of time being separated by a time interval during which composition to be sterilized is not irradiated with microwaves.

7. A process as claimed din claim 1, wherein said oligomers consist essentially of the residues of monomers selected from the group consisting of lower hydroxycarboxylic acids, salts thereof, alcohols, carboxylic acids other than lower hydroxycarboxylic acids, and mixtures thereof.

8. A process as claimed in claim 2, wherein said oligomers consist essentially of residues of (i) monomers selected from the group consisting of glycolic acid, lactic acid, derivatives thereof, and mixtures of any two or more of these components and (ii) monomers selected form the group consisting of alcohols other than hydroxycarboxylic acids, carboxylic acids others than hydroxycarboxylic acids, and mixtures thereof.

9. A process as claimed din claim 8, wherein said composition is sterilized while contained in an at least substantially sealed pack.

10. A process as claimed in claim 7, wherein said composition is sterilized while contained in an at lest substantially sealed pack.

11. A process as claimed in claim 2, wherein said composition is sterilized while contained in an at least substantially sealed pack.

12. A process as claimed in claim 11, wherein the composition that is sterilized by the process is viscous and free-flowing in the sterilization temperature range.

13. A process as claimed in claim 10, wherein the composition that is sterilized by the process is viscous and free-flowing in the sterilization temperature range.

14. A process as claimed in claim 9, wherein the composition that is sterilized by the process is viscous and free-flowing in the sterilization temperature range.

15. A process as claimed din claim 8, wherein the composition that is sterilized by the process is viscous nd free-flowing in the sterilization temperature range.

16. A process as claimed in claim 7, wherein the composition that is sterilized by the process is viscous and free-flowing in the sterilization temperature range.

17. A process as claimed in claim 3, wherein the composition that is sterilized by the process is viscous and free-flowing in the sterilization temperature range.

18. A process as claimed in claim 2, wherein the composition that is sterilized by the process is viscous and free-flowing in the sterilization temperature range.

19. A process as claimed in claim 8, wherein the composition to be sterilized is continuously irradiated with microwaves for each of at lest two distinct periods of time, said periods of time being separated by a time interval during which the composition to be sterilized is not irradiated with microwaves.

20. A process as claimed in claim 7, wherein the composition to be sterilized is continuously irradited with microwaves for each of at least two distinct periods of time, said periods of time being separated by a time interval during which composition to be sterilized is not irradiated with microwaves.

* * * * *